(12) United States Patent
Johnson et al.

(10) Patent No.: US 7,434,446 B2
(45) Date of Patent: Oct. 14, 2008

(54) SYSTEM FOR THE TRANSFER AND SENSING OF GAS DISSOLVED IN LIQUID UNDER PRESSURE

(75) Inventors: Bruce Johnson, Halifax (CA); Craig McNeil, Narragansett, RI (US)

(73) Assignee: Pro-Oceanus Sytems, Inc., Nova Scotia (CA)

( * ) Notice: Subject to any disclaimer, the term of this patent is extended or adjusted under 35 U.S.C. 154(b) by 239 days.

(21) Appl. No.: 10/954,949

(22) Filed: Oct. 1, 2004

(65) Prior Publication Data
US 2006/0070525 A1    Apr. 6, 2006

(51) Int. Cl.
*G01N 33/18* (2006.01)
*G01D 19/00* (2006.01)

(52) U.S. Cl. .................. 73/19.1; 73/19.05; 73/863.23; 96/6

(58) Field of Classification Search ............... 73/19.05, 73/863.71, 863.81, 864.73, 19.1, 863.23, 73/864.33; 96/4–11
See application file for complete search history.

(56) References Cited

U.S. PATENT DOCUMENTS

| | | | | |
|---|---|---|---|---|
| 3,834,546 A | * | 9/1974 | Brun et al. ............. | 210/321.87 |
| 4,702,102 A | * | 10/1987 | Hammerton ................. | 73/19.1 |
| 5,121,627 A | * | 6/1992 | D'Aoust ..................... | 73/19.05 |
| 5,655,529 A | * | 8/1997 | Pontzer ....................... | 600/365 |

\* cited by examiner

Primary Examiner—Daniel S Larkin
(74) Attorney, Agent, or Firm—Miltons LLP

(57) ABSTRACT

A gas separation system for extraction of gas from pressurized fluid has a gas sampling interface and gas circulation tubing to pass sampled gas to a gas sensor to determine the character or a property of the gas. The gas sampling interface includes a semi-permeable membrane in the form of tubing having an inner core volume with an internal support that provides multiple supporting surfaces to prevent collapse of the tubing wall against external pressure and provides interstitial spaces for the flow of gas. Internal supports may include a coil of spring-like configuration fitted coaxially within the tubing; or multiple filaments that form a longitudinal bundle within the core of the tubing, or both. An outer tubular conduit surrounding the semi-permeable membrane tubing provides a flow path for the external fluid to increase the rate of diffusion of dissolved gases through the semi-permeable membrane.

20 Claims, 3 Drawing Sheets

SYSTEM FOR THE TRANSFER AND SENSING OF GAS DISSOLVED IN LIQUID UNDER PRESSURE

FIELD OF THE INVENTION

This invention relates to the separation of a gas from a liquid and to the mass transfer of a gas present within a liquid in a high-pressure environment into a low pressure environment. More particularly, it relates to the detection of the presence of gas within a liquid and, in particular to sampling, identifying the character or property, and quantifying the amount and/or partial pressure of gas dissolved in fluids liquids under pressure, including in water at depth in the water column of the ocean or a river or lake, or in water or other liquid confined in a pressure vessel in industrial process or storage applications.

Further, it relates to the use of the pressure-resistant membrane of the system to achieve the mass transport of a gas into, or out of, solution with a liquid under pressure.

BACKGROUND TO THE INVENTION

In the field of oceanography, it is often desired to obtain a direct measurement of the identity and pressure of dissolved gases present in seawater or freshwater. A major target gas is carbon dioxide —$CO_2$. Known techniques for obtaining such measurements include the use of semi-permeable membranes that allow such gases to penetrate into a sampling volume, while resisting the penetration of the external liquid and sustaining the hydrostatic pressure so that it does not collapse the sampling volume.

Samples of prior art techniques for measuring the partial pressure of gases, and particularly carbon dioxide dissolved in seawater, are respectively European patents EP-01 04 35 85 A2 and EP-00 59 26 32 A1. An example of a planar membrane which is supported in order to resist hydrostatic pressure is described in U.S. Pat. No. 5,121,627. The support of the planar geometry of a membrane against substantial hydrostatic pressures, while preserving structural integrity and semi-permeability of the membrane, is difficult, and is impracticable in applications where a relatively large total area of membrane is required for an acceptably high rate of penetration of the gas under detection into the sampling volume, with corresponding enhancement of response time performance.

Use of semi-permeable membranes in the format of tubing is described in U.S. Pat. Nos. 3,871,228; 4,563,892, and 4,662,210. An advantage of the use of tubing is that, particularly in respect of smaller diameter tubing, the curved walls of semi-permeable membrane material can be largely self-supporting, at least at lower pressures. Thus, the area limitations of the planar membrane can be overcome, in that the surface of the tubular membrane forms the effective area for penetration of gas into the interior volume, and may be increased proportionally by the length of the tubing comprising the membrane.

However, at higher hydrostatic pressures, the semi-permeable material forming the tubular membrane does not have sufficient mechanical strength to resist the external pressure and will undergo collapse to close the interior space such that the penetration of the gas and its transfer to the detection instrumentation is obstructed. It is also known that to create a optimal system for the detection and measurement of gas by penetration of the gas from a liquid through a semi-permeable membrane into a sample space, the volume of the sample space must be relatively small in relation to the active membrane area to achieve reasonably rapid equilibration of the gas in the sample space with the ambient liquid from which it was derived, thereby shortening the response time of the instrumentation.

In U.S. Pat. No. 5,763,762, it is suggested that a filler for the purpose of reducing the internal volume of a tubular semi-permeable membrane may be provided from the group: thread, mono-filament, powder, wire, in situ formed polymer, fluid and any combination of these. However, U.S. Pat. No. 5,763,762, does not discuss as a design consideration, the utility of a system for the detection or measurement of a gas dissolved in liquid under pressure, or the incorporation of the feature of a pressure resistance membrane as an element of the invention claims.

Fillers of the type previously proposed will have a tendency to permit partial or complete collapse of the tubing, the compression and constriction of the filler substrate, or the rendering the membrane susceptible to mechanical penetration or rupture by the forcing of the membrane film into voids in the filler substrate or projections on filler elements, thereby increasing the pressure drop occurring when sampled gas is removed from the core of such tubing or rendering the system non-functional.

Further, in order to shorten the response time of such a system, it is desirable for the gases present in the external liquid to be exposed to the semi-permeable membrane with minimal interference from boundary layers that are depleted in such gases.

The invention addresses the objects of overcoming the disadvantages of the prior art and provides for a new form of gas detection and transfer system that operates with a minimized response time.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

According to the present invention, in one aspect an gas transfer or detection system relies on a semi-permeable membrane in the format of tubing which contains an internal support. According to one embodiment, the internal support presents multiple, generally cylindrical, supporting surfaces to the inside wall of the tubing. Such multiple cylindrical supporting surfaces may be provided by a coil of spring-like configuration fitted coaxially within the tubing. Alternately, such multiple cylindrical supporting surfaces may be provided by multiple filaments that form a longitudinal bundle within the core of the tubing.

Both variants of the invention enable use of a relatively thinner wall in the tubing which serves as a semi-permeable membrane. Both variants act by providing support for the inner wall of such tubing. An advantage of the use of the coil-format variant is that gas samples may be removed from the inner core of the coil rapidly with minimum pressure drop. An advantage of the use of the filament format of the invention is that the sampling volume present inside the tubing, in the interstitial spaces between the filaments, is reduced in size.

In both cases, in the gas detection mode gas circulation means may be used to pass sample gas present within the tubing to the gas sensor or detector present within the instrument. Such sensor may determine the pressure of the gas in the gas sampling volume. It may also determine the character or property of such gas, for example and without constituting a limitation, identifying the presence of dissolved oxygen or carbon dioxide or distinguishing between the partial pressures of different categories of gases present in the gas sampling volume, corresponding to the dissolved gases present in the external liquid.

To enhance the response of the instrument to changes in ambient dissolved gases, the semi-permeable membrane tubing may be surrounded by an outer, preferably co-axial, tubular conduit or channel through which the external liquid is forced to follow. By imposing a flow rate on such external liquid, the boundary layer of gas-depleted liquid adjacent the semi-permeable membrane is reduced in thickness. This hastens the mass transfer rate of gas from the liquid through the semi-permeable membrane, shortening the response time of the instrument.

According to a further variant, the liquid in the outer tubular conduit is forced to follow a spiral path around the semi-permeable membrane tubing. This spiral path may be imposed, for example, by placing a spiral baffle on the outer wall of the membrane or the inner wall of the outer tubular conduit. In a specific embodiment of this variant, the spiral baffle may be created by a copper wire in the form of an expanded spring of diameter approximately equal to the annular space between the outer tubular conduit and the semi-permeable membrane tubing within such conduit. Copper is preferred as being toxic to microorganisms that would otherwise foul the outer surface of the semi-permeable membrane.

The foregoing summarizes the principal features of the invention and some of its optional aspects. The invention may be further understood by the description of the preferred embodiments, in conjunction with the drawings, which now follow.

DESCRIPTION OF THE PREFERRED EMBODIMENT

Figure 1:
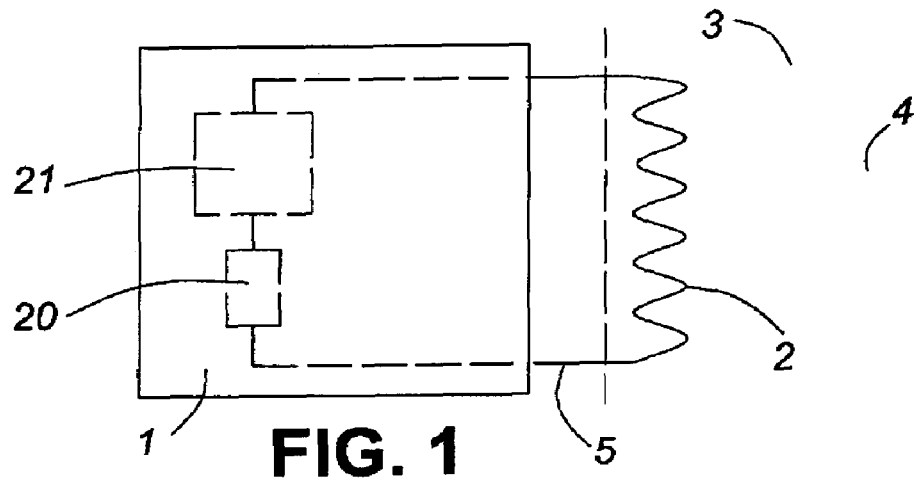
FIG. 1 is a schematic diagram of the sensor package including a gas circulation means to pass gas present within the cylindrical membrane interface to the gas sensor present within the instrument.

FIG. 1 is a schematic depiction of the sensor package 1 and tubular membrane interface 2 which has been immersed into a liquid phase 3 containing dissolved gas 4. Connecting tubing 5 extends between the membrane interface 2 and the sensor package 1. The sensor package 1 includes a sensor capable of measuring a component or property of the gas that is sampled by the membrane interface 2. For example, the entire system may be submerged as in an underwater instrument or the sensor package 1 may be above water or in a laboratory.

The membrane interface 2 may be attached to the sensor package 1 at only one end, relying on diffusion to communicate with the sensor package 1. Alternately, for flow-through applications, the tubular membrane interface 2 may be coupled at both ends to the sensor package 1. Further, the tubular membrane interface 2 may be in the form of multiple tubings which are interconnected or connected at a manifold. In the case of a flow-through configuration, both ends may be closed during equilibration whereby the membrane interface 2 acts as a known volume sample loop.

Examples for the sensor are a pressure sensor, a gas chromatograph, a mass spectrometer, an optical cell or any other sensor that measures a property of the one or more captured gases. The sensor of the sensor package 1 may also be incorporated into the actual tubular membrane interface 2, as in the case where the system comprises an optical cell.

Substances to be sampled will typically be gases that will equilibrate across or pass through the interface between liquid phase and the inner core volume 6 of the tubular membrane interface 2 which serves as a sample gas circulation volume. The system applies to any substance that can be made to pass through the interface that serves as a barrier for other substances, and equilibrate, or otherwise be detected or measured, even if not equilibrated.

Figure 2:
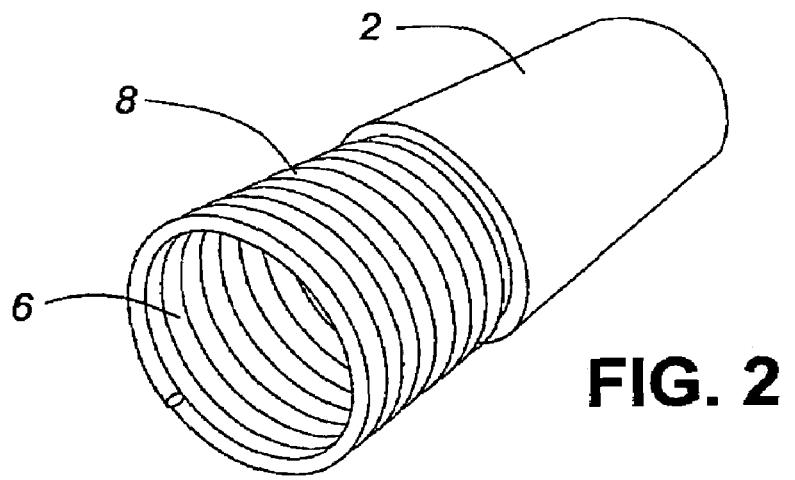
FIG. 2 is a perspective view of the cylindrical membrane with detail of the wire coil spring internal support.

FIG. 2 depicts a tubular membrane interface 2 supported by a support member 7 in the form of a spiral coil 8. The spiral coil 8 may be made of wire or any equivalent material. The wire in such spiral coil 8 need not be necessarily round, but could be of any cross-section, e.g. square or spiral in cross-section, which is effective for the application. It is in this most generalized sense that such support members are "cylindrical". The spiral should be wound sufficiently tightly as to preclude the collapse of the tubular membrane 2 into gaps between consecutive coils.

Figure 3:
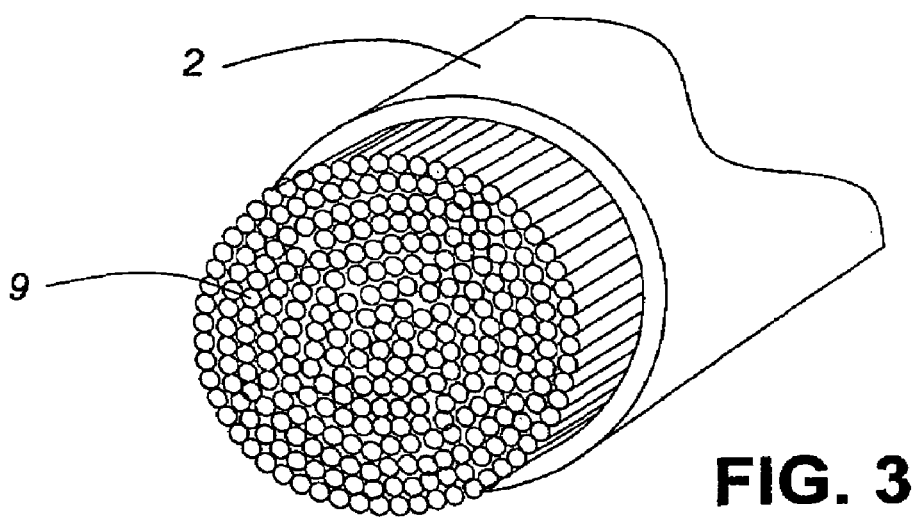
FIG. 3 is a perspective view of the cylindrical membrane with detail of the longitudinal filament bundle internal support having interstitial spaces between adjacent filaments.

FIG. 3 depicts a tubular membrane interface 2 supported by an alternate support member 7 in the form of a wire bundle 9. While referred to as "wire", these elements need not be made of metal, and any equivalent functioning form of filament maybe employed. The wire bundle 9 will typically be composed of large numbers of fine wires. The wires may be in patterned in groups, i.e., twisted bundles of multiple wires, or may be packed individually. The wires in such bundles 9, as with the wires of the spiral coil 8, need not be necessarily round, but may be of any cross-section, e.g. square or spiral, which is effective for the application. The multiple filaments that form a wire bundle 9 contain longitudinal channels that provide interstitial spaces between adjacent filaments of the longitudinal bundle for the flow of gas within the inner core volume 6 which serves as a sample gas circulation volume.

Both wire bundle-supported and coil spring-supported supports 7 may be of any length, but have been found to provide useful sampling interfaces in lengths of a few centimeters to several meters. Both coiled spring 8 supported and wire bundle 9 supported types of interfaces have been shown to provide proof against pressures in excess of 600 PSI, maintaining resistance against this pressure for periods of weeks.

Use of supported semi-permeable interfaces of the invention is not limited to applications involving high external liquid pressures, but may also find application in cases where the interior of the interface has been evacuated. Further, interfaces according to the invention may be employed where the object is to introduce a high-pressure gas into a liquid under lower pressure. In such case, the liquid flows through the central core volume of the tubular membrane interface, and the gas is present in the exterior environment.

Difficulty may attend the covering of the coiled spring support 8 with the tubular semi-permeable membrane 2. The tubular membrane 2 will need to be stretched over the coil spring support 8 in order to avoid excessive pressure increases inside the interface when the liquid pressure increases outside. The coiled spring 8 may be forced inside of the tubular membrane 2 by sliding, and this can be assisted with addition of lubricant such as soap or even water. However, this approach to fabrication may often result in a damaged membrane. Other methods of inserting the coiled spring 8 may also include pressurizing the inside of the tubular membrane 2 with air or water to increase the internal diameter of the membrane so that the coiled spring 8 can be inserted therein.

One particularly effective means of fabricating the coiled spring supported interface involves inserting the coiled spring 8 into a tubular membrane interface 2 made of elastically resilient material that, in its relaxed condition has an inside diameter which is larger than the outside diameter of the coiled spring 8. Then, by stretching the over-sized tubular membrane 2 longitudinally the diameter of the oversized tubular membrane 2 will decrease and can be made to fit tightly against the outside diameter of the spring 8. An added advantage of this method of assembly is that the thinning of the membrane wall of the tubular membrane 2 will enhance the rate of mass transfer of gases through such membrane wall.

Using this technique, a typical fabrication might include stretching silicone tubing of size 0.055" ID over a spring of 0.039" OD. With this particular interface the starting silicone tube 2 length is chosen to be ½ to ⅔ of the spring length. Stretching the tubing 2 longitudinally to the length of the spring 8 then causes the inside diameter of the tubing 2 to conform to the outside diameter of the spring 8. The thinning of the wall is illustrated by one assembly in which a silicone cube 2 with a wall thickness of 0.030" was stretched to two times its relaxed length and in so doing decreased in wall thickness to 0.013".

Figure 4:
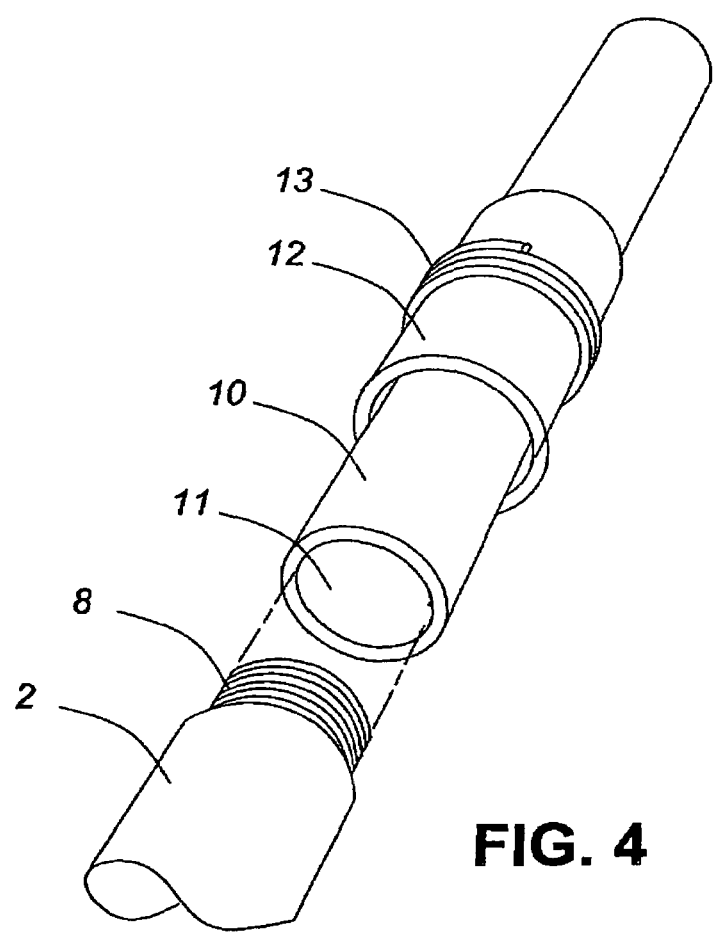
FIG. 4 is a diagram of the connection between the cylindrical membrane interface and the tubing from the sensor package.

Terminations on the ends of the tubular membrane interfaces 2 are intended to provide the same strength and resistance against compression as the supported membrane, and without introducing significant impediment to gas flow. One method for providing this termination, as depicted in FIG. 4, is to drill rigid (usually metal although may be plastic, or other material) interface tubing 10 and insert the end of the coil spring 8 about 1 centimeter into this drilled hole 11. Then, the semi-permeable membrane tubing 2 is pushed at least one centimeter over the outside of the drilled metal or plastic tubing 10. Another piece of silicone-type or other flexible tubing 12 (here called the "flexible termination tubing") with an inside diameter smaller than the outside diameter of the interface tubing 10 is stretched to slip over the joint such that this piece of flexible termination tubing 12 covers at least one centimeter of the coiled spring 8 supported interface on one end.

This flexible termination tubing 12 spans the joint at one end and then, at the other end, covers several centimeters of the rigid metal or plastic interface tube 10. External wire 13 or a similar filament is then wrapped around this outer, flexible termination tubing 12 where it covers the rigid tubing 10. A final layer of heat-shrink tubing (not shown in FIG. 4) is applied over the termination such that the heat shrink tubing completely covers and overlaps the external wire 13 or similar filament, and the ends of the flexible termination tubing 12. Both ends of the interface are treated in the same manner. The result is a supported interface with rigid tubing at the ends for connection via e.g., Swagelok or other means to an appropriation sensor package 1.

In order to improve the rate of equilibration across the liquid/gas interface, it has been found useful to force the external liquid e.g. water, to flow adjacent to the tubular semi-permeable membrane interface 2 in intimate contact with its outside surface. Equilibration of one such interface improved from a time constant of two minutes to a time constant of fifteen seconds when such a flow was imposed. One method of imposing intimate flow adjacent the outside surface of the tubular membrane interface is to place such interface 2 tubing inside a larger diameter flow-control cylinder or flow confinement structure 14, and then pump liquid to be sampled through the annular space 15 so formed. The flow path for the liquid induced by this cylinder 14 can be formed within any solid body.

Figure 5:
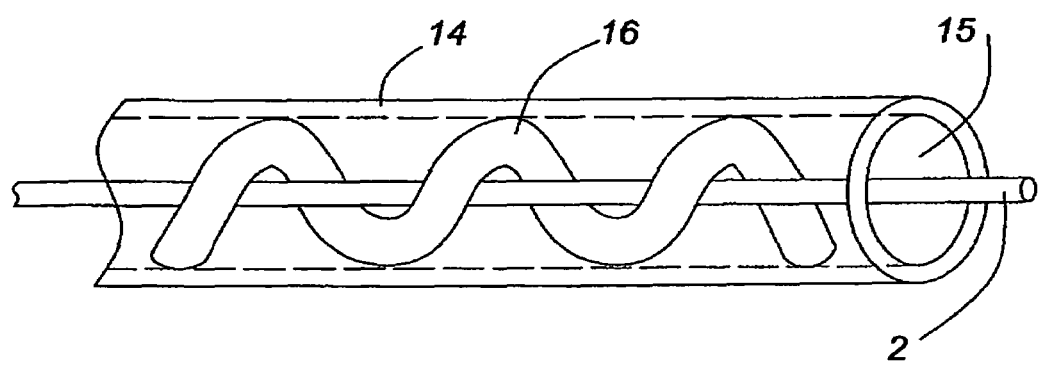
FIG. 5 is a diagram of the spiral baffle between the cylindrical membrane interface and the outer conduit tubing.
Figure 6:
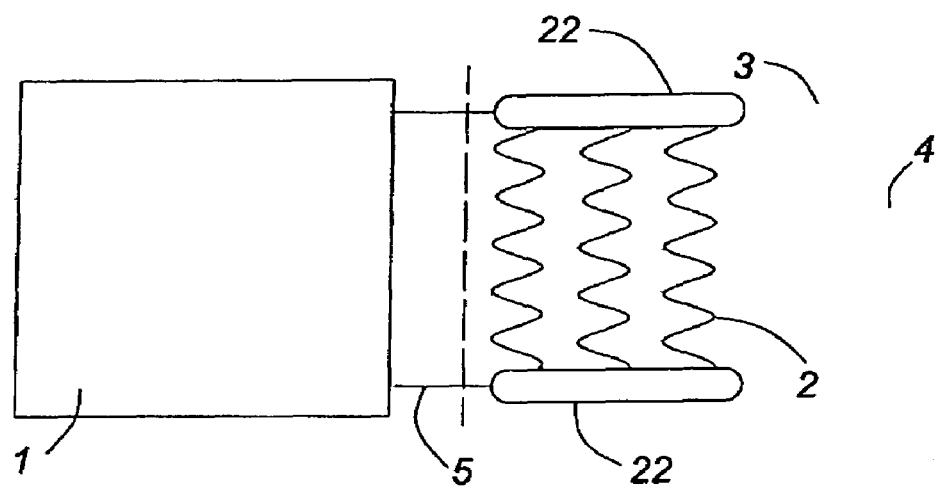
FIG. 6 is a schematic diagram of the sensor package of FIG. 1 incorporating multiple gas absorption means operating through a manifold.

One challenge arising in this method is keeping the tubular membrane interface near the center of the flow channel. This can be done by placing a helical baffle 16 (for example a copper wire) on the inside wall of the flow tube 14. This feature is shown in FIG. 5. As depicted, the helical baffle 16 fills the width of the annular space 15. Such a helical baffle 16 need not fill the entire width of the annular space 15, although this would be preferable. It is sufficient for it to induce a spiral flow path in the liquid. By this means pumped liquid is then forced to swirl around the annular gap 15 and provide a highly efficient mass transfer. Further, effective mass transfer of the gas through the cylindrical membrane interface 2 can be achieved by forming a channel in the flow confinement structure 14 to receive the helical baffle. Thus, such channel can be cut into the surface of a supporting body 14 whereby the liquid is confined within such channel.

It is desirable to maintain the flow conduit 14 generally coaxial with the cylindrical semi-permeable membrane 2. Where the helical baffle 16 is not of sufficient depth to maintain such generally co-axial position of the flow conduit 14 it may be necessary to provide spacing lugs on the inside surface of the flow conduit to preserve the co-axial position of the cylindrical membrane 2.

It has been found useful to coil the resulting assembly around a forming spool to create a larger spiral, increasing the density of the assembly in a manner similar to that present in DNA. Increased compactness for the assembly can also be achieved by inserting it into a channel that is fabricated as part of the instrument housing. The radius of curvature of the assembly should be kept large enough to avoid spreading the internal supporting coiled spring 8 and thereby weakening the support provided to the tubular membrane interface 2. For a tubular membrane interface 2 supported by a 0.039" diameter spring, a radius of curvature of about 3" appears sufficient to avoid this problem.

It is also possible to reduce the inner core volume 6 within a spirally supported tubular membrane interface 2 by insertion of a monofilament filler within such inner core. A filled-core system is more appropriate for measurements of gas pressure. Flow-through systems, e.g., for measuring other parameters of specific gases, are usually better served when the dead volume is unobstructed. Typical results for employment of a monofilament filler in a spring-supported tubular membrane interface in a system that directed to measuring partial gas pressure are reported as follows:

A 0.039" OD spring with ID 0.019" was covered with a silicone tube of 0.059" ID with 0.010" thick wall. The tubing 2 was then stretched in length to tighten in diameter around the spring 8. A pressure sensor with dead volume of 0.3 cm$^3$ was attached to the interface at one end and the other end of the interface was closed off. Eight feet of the supported tubular membrane interface 2 was then placed inside a ⁵⁄₁₆" ID external plastic tube 14 and water pumped at the rate of one gallon per minute through the annular space 15 around the interface. At time zero, one liter of degassed water was mixed into the tank of air-saturated water. The time constant for equilibration of the interface/pressure sensor was measured to be 3.5 minutes without monofilament inside the spring 8 interface. With 0.013" monofilament occupying dead volume within the inner core volume 6 the time constant was 1.8 minutes.

However, filling the interface with a larger diameter filler (e.g. 0.016" monofilament) actually resulted in a longer time constant for equilibration. This effect may arise because the resistance to gas flow through the interface increased.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

The embodiments of the invention in which an exclusive property or privilege is claimed are defined as follows:

1. In a gas sensing system for measuring the character or a property of a gas dissolved in water at depth in the water column of the ocean or a river or lake, or of water or other liquid confined in a pressure vessel in an industrial process or storage application, the combination of:
   i) a gas sensor for detecting a characteristic or property of at least one gas presented to said sensor,
   ii) a gas absorption means for effecting the transfer of gas dissolved in said water or other liquid under pressure into a sample gas volume to provide sample gas, and
   iii) the sample gas volume being connected to pass gas present therein to the gas sensor through sample gas circulation tubing;
   said gas absorption means comprising:
   a) a semi-permeable membrane admitting the transfer of gas while substantially excluding the penetration of liquid, such membrane being in the form of tubing having an outside surface, a tubing wall, an inside tubing wall surface and an inner core volume; and
   b) an internal support present within the inner core volume, the internal support having multiple spaced supporting surfaces which are presented to the inside tubing wall surface to provide support for said tubing wall against a pressure differential existing between the exterior of the tubing wall and the inner core volume,
   c) wherein the sample gas circulation tubing communicates with the inner core volume of said gas absorption means for carrying sample gas present therein to said gas sensor, whereby gas dissolved in the liquid when present outside the tubing wall having the outside surface may pass through said tubing wall into the inner core volume and be transported by the sample gas circulation means to the gas sensor for detection of the gas that has passed through the tubing wall.

2. A gas sensing system as in claim 1 wherein said internal support comprises a coil of spiral spring-like configuration wound sufficiently tightly to preclude the collapse under pressure of the tubular membrane between consecutive coils and fitted coaxially within the tubing to provide space for the flow of gas within the inner core volume of the membrane, the coil having an inner coil passage with open ends for communication of sample gas to the gas sensor.

3. A gas sensing system as in claim 1 wherein said internal support comprises multiple filaments that form a longitudinal bundle containing longitudinal channels that provide interstitial spaces between adjacent filaments of the longitudinal bundle for the flow of gas within the inner core volume.

4. A gas sensing system as in any one of claims 1, 2 and 3 wherein the membrane of the tubing wall is under longitudinal tension.

5. A gas sensing system as in claim 1 wherein said sensor determines the partial pressure of at least one gas present in the inner core volume.

6. A gas sensing system as in claim 1 wherein the gas absorption means comprises multiple gas absorption means which are interconnected through a manifold to the sample gas circulation means.

7. A gas absorption means for affecting the transfer of gas dissolved in a liquid under pressure comprising:
   a) a semi-permeable membrane admitting the transfer of gas while substantially excluding the penetration of liquid, such membrane being in the form of tubing having an outside surface, a tubing wall, an inside tubing wall surface and an inner core volume; and
   b) an internal support present within the inner core volume, the internal support having multiple spaced supporting surfaces which are presented to the inside tubing wall surface to provide support for said tubing wall against a pressure differential existing between the exterior of the tubing wall and the inner core volume,
   whereby gas dissolved in the liquid when present outside the tubing wall may pass through the tubing wall into the inner core volume, and further comprising, to enhance the response of the gas absorption means to changes in ambient dissolved gases and:
   c) an outer tubular conduit surrounding and connected to the semi-permeable membrane tubing and providing a flow path for the liquid to follow that is adjacent to the outside surface of said semi-permeable membrane tubing,
   whereby liquid may be caused to pass along said flow path and thereby increase the rate of mass transfer of dissolved gases through the semi-permeable membrane.

8. A gas absorption means as in claim 7 wherein the flow path is an annular flow path and wherein said annular flow path comprises a hectically formed baffle to define such flow path.

9. A gas absorption means as in claim 8 wherein the helically formed baffle has a width that occupies the space between the outer tubular conduit and said semi-permeable membrane tubing.

10. A gas absorption means as in claim 9 wherein the hectically formed baffle comprises copper wire so as to be toxic to microorganisms that would otherwise foul the outer surface of the semi-permeable membrane.

11. A gas absorption means as in claim 7 wherein said internal support comprises a coil of spring-like configuration wound sufficiently tightly to preclude the collapse under pressure of the tubular membrane between consecutive coils and fitted coaxially within the tubing to provide space for the flow of gas within the inner core volume.

12. A gas absorption means as in claim 7 wherein said internal support comprises multiple filaments that form a longitudinal bundle containing longitudinal channels that provide interstitial spaces between adjacent filaments of the longitudinal bundle for the flow of gas within the inner core volume.

13. A gas absorption means as in any one of claims 7, 8, or 9 wherein the membrane of the tubing wall is under longitudinal tension.

14. A gas transfer system for affecting the transfer of gas under pressure comprising:
   a) a semi-permeable membrane admitting the transfer of gas while substantially excluding the penetration of liquid, such membrane being in the form of tubing having an outside surface, a tubing wall, and an inside tubing wall surface and an inner core volume, the tubing wall being under longitudinal tension; and
   b) an internal support present within the inner core volume, the internal support having multiple spaced supporting surfaces which are presented to the inside tubing wall surface to provide support for said tubing wall against a pressure differential existing between the exterior of the tubing wall and the inner core volume,
whereby gas present under a given pressure outside the tubing wall may pass through the tubing wall into the inner core volume when the inner core volume is at a pressure that is lower than the given pressure.

15. A gas transfer system as in claim 14 wherein said internal support comprises a coil of spiral spring-like configuration wound sufficiently tightly to preclude the collapse under pressure of the tubular membrane between consecutive coils and fitted coaxially within the tubing to provide space for the flow of gas within the inner core volume.

16. A gas transfer system as in claim 14 wherein said internal support comprises multiple filaments that form a longitudinal bundle containing longitudinal channels that provide interstitial spaces between adjacent filaments of the longitudinal bundle for the flow of gas within the inner core volume.

17. A gas transfer system as in any one of claims 14, 15 or 16 further comprising:
   a) an outer tubular conduit surrounding the semi-permeable membrane tubing and providing a flow path for the liquid to follow that is adjacent to the outside surface of said tubing; and,
whereby the fluid may be caused to pass along said flow path and thereby increase the rate of mass transfer of dissolved gases through the semi-permeable membrane.

18. A gas transfer system as in claim 17 wherein the flow path is an annular flow path and wherein said annular flow path comprises a hectically formed baffle present therein that occupies the space between the outer tubular conduit and said tubing.

19. A gas transfer system as in claim 18 wherein the helically formed baffle comprises copper wire so as to be toxic to microorganisms that would otherwise foul the outer surface of the semi-permeable membrane.

20. A method for installing a semi-permeable, tubular, gas transfer membrane having a tubing wall and an inner core volume with an inside diameter over an internal support in the form of a coil of spring-like configuration with an outside diameter to be fitted within the inner core volume, comprising the steps of:
   a) selecting a tubular membrane of elastically resilient material that, in its relaxed condition, has an inside diameter which is larger than the outside diameter of the coil of spring-like configuration and therefore constitutes an over-sized tubular membrane;
   b) inserting the coil within the inner core volume of the tubular membrane;
   c) stretching the over-sized tubular membrane longitudinally over the coil and thinning the membrane wall until the diameter of the oversized tubular membrane has decreased to conform to the outside diameter of the coil of spring-like configuration with the tubing wall being under longitudinal tension; and
   d) fixing the ends of the membrane so as to retain the membrane in place over the coil in a condition of longitudinal tension.

* * * * *

UNITED STATES PATENT AND TRADEMARK OFFICE
CERTIFICATE OF CORRECTION

| | | |
|---|---|---|
| PATENT NO. | : 7,434,446 B2 | Page 1 of 1 |
| APPLICATION NO. | : 10/954949 | |
| DATED | : October 15, 2008 | |
| INVENTOR(S) | : Bruce Johnson and Craig McNeil | |

It is certified that error appears in the above-identified patent and that said Letters Patent is hereby corrected as shown below:

Column 1, line 13 the word "fluid" should be deleted

In claim 1, column 7, line 58 "c)" is to be deleted

Signed and Sealed this

Seventh Day of July, 2009

JOHN DOLL
*Acting Director of the United States Patent and Trademark Office*